(12) United States Patent
Lee et al.

(10) Patent No.: US 8,995,612 B2
(45) Date of Patent: Mar. 31, 2015

(54) IMAGE DIAGNOSIS APPARATUS AND METHOD USING X-RAY

(75) Inventors: Jong Ha Lee, Hwaseong-si (KR); Dong Goo Kang, Suwon-si (KR); Sung Su Kim, Yongin-si (KR); Young Hun Sung, Hwaseong-si (KR); Seok Min Han, Bundang-gu (KR); Kwang Eun Jang, Busan-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 508 days.

(21) Appl. No.: 13/067,160

(22) Filed: May 12, 2011

(65) Prior Publication Data

US 2011/0311020 A1    Dec. 22, 2011

(30) Foreign Application Priority Data

Jun. 22, 2010    (KR) .................. 10-2010-0058907

(51) Int. Cl.
*A61B 6/04*    (2006.01)
*A61B 6/00*    (2006.01)
*A61B 6/02*    (2006.01)

(52) U.S. Cl.
CPC .................. *A61B 6/0414* (2013.01); *A61B 6/48* (2013.01); *A61B 6/025* (2013.01)
USPC .............................. 378/37; 378/62

(58) Field of Classification Search
USPC ...................................... 378/37, 62
See application file for complete search history.

(56) References Cited

U.S. PATENT DOCUMENTS

| | | |
|---|---|---|
| 2003/0095624 A1 | 5/2003 | Eberhard et al. |
| 2008/0043904 A1 | 2/2008 | Hoernig |
| 2009/0010384 A1* | 1/2009 | Jing et al. .......... 378/37 |
| 2009/0022264 A1* | 1/2009 | Zhou et al. .......... 378/5 |
| 2009/0268866 A1* | 10/2009 | Hoheisel .......... 378/37 |
| 2011/0222653 A1* | 9/2011 | Virta .............. 378/37 |

FOREIGN PATENT DOCUMENTS

| | | |
|---|---|---|
| EP | 1 759 637 A2 | 3/2007 |
| JP | 2003-180657 | 7/2003 |
| KR | 10-2008-0030745 | 4/2008 |
| WO | 2004/049949 A1 | 6/2004 |

* cited by examiner

*Primary Examiner* — Hoon Song
(74) *Attorney, Agent, or Firm* — Harness, Dickey & Pierce, P.L.C.

(57) ABSTRACT

An image diagnosis apparatus and method may emit radiation to a target object, may compress the target object in response to the emitted radiation, and may collect a plurality of images with respect to the compressed target object in response to the emitted radiation. An elastic image with respect to the target object may be generated based on the plurality of collected images.

20 Claims, 6 Drawing Sheets

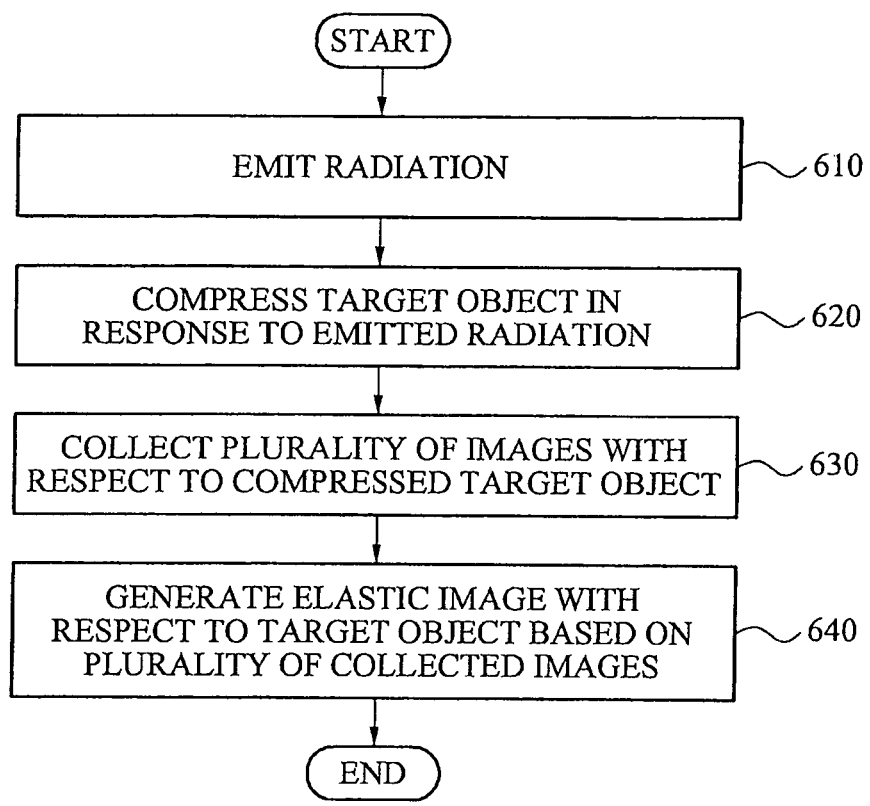

IMAGE DIAGNOSIS APPARATUS AND METHOD USING X-RAY

CROSS-REFERENCE TO RELATED APPLICATIONS

This application claims the benefit of Korean Patent Application No. 10-2010-0058907, filed on Jun. 22, 2010, in the Korean Intellectual Property Office, the disclosure of which is incorporated herein by reference.

BACKGROUND

1. Field

One or more embodiments relate to an image diagnosis apparatus and method that may emit radiation to a target object, may compress the target object in response to the emitted radiation, may collect a plurality of images with respect to the compressed target object, and may generate an elastic image based on the plurality of collected images.

2. Description of the Related Art

Tissues constituting a target object may be classified into hard tissue and soft tissue. When the hard tissue, such as bone and the like, exists, an image quality may be deteriorated due to an overlap between the hard tissue and other tissue located behind the hard tissue. Also, a component ratio of the hard tissues, such as bone and the like, is irregular and thus, the overlap may not be completely overcome.

Currently, a technology based on a computed tomography (CT) or a non-destructive inspector may be used to detect cancer tissue.

Cancer tissue is classified as soft tissue, and thus, tomography may be effectively used for a breast cancer test. Cancer tissue may be detected based on an image showing a change in density of substances constituting a breast, and the image may be obtained by compressing the breast in a direction from a top to a bottom or compressing the breast in a direction from inside to outside.

A non-destructive inspection based on an X-ray may be used to detect a cancer.

X-ray is mainly used to detect a cancer and thus, there is a need for a system having a high sensitivity. However, in real clinical testing, a system having a high specificity in addition to high sensitivity may be needed. An invasive biopsy, which detects whether a lesion is benign or malignant, may adversely affect a patient. Thus, it may be important that an X-ray image obtaining and image processing system detects only a malignant lesion from human tissues.

SUMMARY

According to an aspect of this application, there is provided an image diagnosis apparatus, the apparatus including an irradiator to emit radiation to a target object, a target object compression unit to compress the target object in response to the emitted radiation, an image collector to collect a plurality of images with respect to the compressed target object, in response to the emitted radiation, and an elastic image generator to generate an elastic image with respect to the target object, based on the plurality of collected images.

According to another aspect of this application, there is provided an image diagnosis method, the method including emitting radiation to a target object, compressing the target object in response to the emitted radiation, collecting a plurality of images with respect to the compressed target object, in response to the emitted radiation, and generating an elastic image with respect to the target object based on the plurality of collected images.

Additional aspects, features, and/or advantages of embodiments will be set forth in part in the description which follows and, in part, will be apparent from the description, or may be learned by practice of the disclosure.

BRIEF DESCRIPTION OF THE DRAWINGS

These and/or other aspects and advantages will become apparent and more readily appreciated from the following description of the embodiments, taken in conjunction with the accompanying drawings of which:

FIG. 6 is a flowchart illustrating an image diagnosis method according to an embodiment.

DETAILED DESCRIPTION

Figure 1:
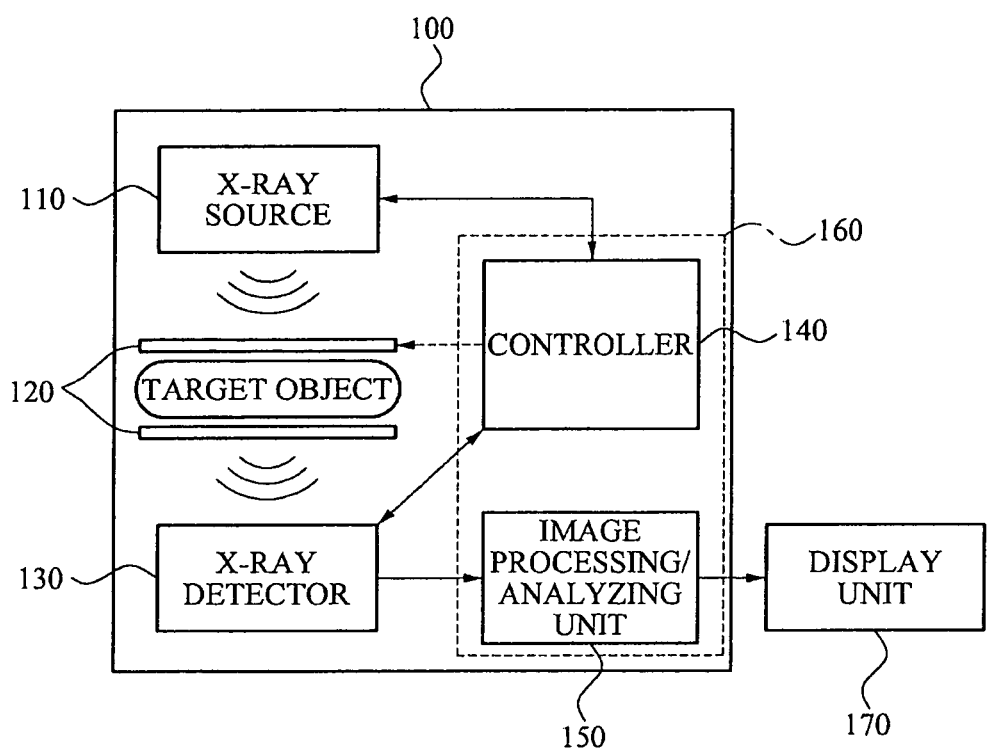
FIG. 1 is a diagram illustrating an X-ray image obtaining and image processing system to which an image diagnosis apparatus is applied according to an embodiment.

Reference will now be made in detail to embodiments, examples of which are illustrated in the accompanying drawings, wherein like reference numerals refer to like elements throughout. Embodiments are described below to explain the present application by referring to the figures.

Throughout the specification, an image diagnosis apparatus using an X-ray may be a system using at least one X-ray source; a system using at least one X-ray detector; or a system using at least one X-ray source and at least one X-ray detector, and may be embodied as one of a radiography system, a tomosynthesis system, a computed tomography (CT), and a non-destructive inspector. Although the image diagnosis apparatus is embodied as one of the radiography system, the tomosynthesis system, the CT, and the non-destructive inspector, these are merely examples and the image diagnosis apparatus may be embodied in various forms and applicable to various application examples.

FIG. 1 illustrates an X-ray image obtaining and image processing system 100 to which an image diagnosis apparatus is applied according to an embodiment.

Referring to FIG. 1, the X-ray image obtaining and image processing system 100 may include an X-ray source 110, a press plate 120, an X-ray detector 130, a controller 140, and an image processing and analyzing unit 150.

The controller 140 and the image processing and analyzing unit 150 may form an image diagnosis apparatus 160.

The X-ray source 110 may emit X-rays to the target object. The X-rays emitted from the X-ray source 110 may include photons having a plurality of energy levels. The X-rays passing through the target object may be detected by the X-ray detector 130. A dose and a voltage of the emitted X-rays and an emission time of the emitted X-rays may be controlled by the controller 140.

The press plate 120 may fix the target object, and the press plate 120 may apply a predetermined compression to the target object in a predetermined direction to compress the target object. Also, the press plate 120 may be configured to remove the applied compression.

The X-ray detector 130 may obtain a plurality of images generated by the emitted X-rays passing through the target object from the X-ray source 110. The X-ray detector 130 may detect X-ray photons projected from the X-ray source 110 to obtain the plurality of images.

When an elastic image generated based on the plurality of images obtained by compressing the target object is used, hard tissue and soft tissue in a human body may be determined and thus, cancer tissue included in the human body may be detected.

The controller 140 may control the X-ray source 110 to enable X-rays to be emitted to the target object based on a predetermined dose and voltage, during a predetermined time period. The controller 140 may control the X-ray source 110 to enable X-rays to be emitted to the target object in a predetermined direction. The controller 140 may control the press plate 120 in response to the control of the X-ray source 110. The controller 140 may adjust a compression intensity of compression of the target object, an X-ray emission angle, an X-ray emission time, and the like.

The image processing and analyzing unit 150 may generate the elastic image from the plurality of collected images with respect to the target object during the predetermined time period, and may perform image processing with respect to the elastic image. The image processing and analyzing unit 150 may perform pre-processing with respect to the elastic image.

As an example of the pre-processing, a region of interest (ROI) to be tested in the target object is predetermined, the ROI is detected from the elastic image, and an elastic image associated with a peripheral region of the detected ROI is separately stored and thus, the separately stored elastic image may be used when an image display is performed. As another example of the pre-processing, a scheme to remove a motion artifact may be adopted, because when the target object is a human body, the motion artifact may be generated due to movement during measurement.

The image processing and analyzing unit 150 may process and form a composite elastic image. The image processing and analyzing unit 150 may detect a changing process with respect to the elastic image generated from the plurality of collected images and thus, may separate substances having different elasticity.

The X-ray image obtaining and image processing system 100 may perform various image processing combinations. The image processing and analyzing unit 150 may generate an elastic image to be used for an analysis based on the image processed elastic images, and the generated elastic image may be outputted from a display unit 170. The image diagnosis apparatus 160 may include the controller 140 and the image processing and analyzing unit 150.

Figure 2:
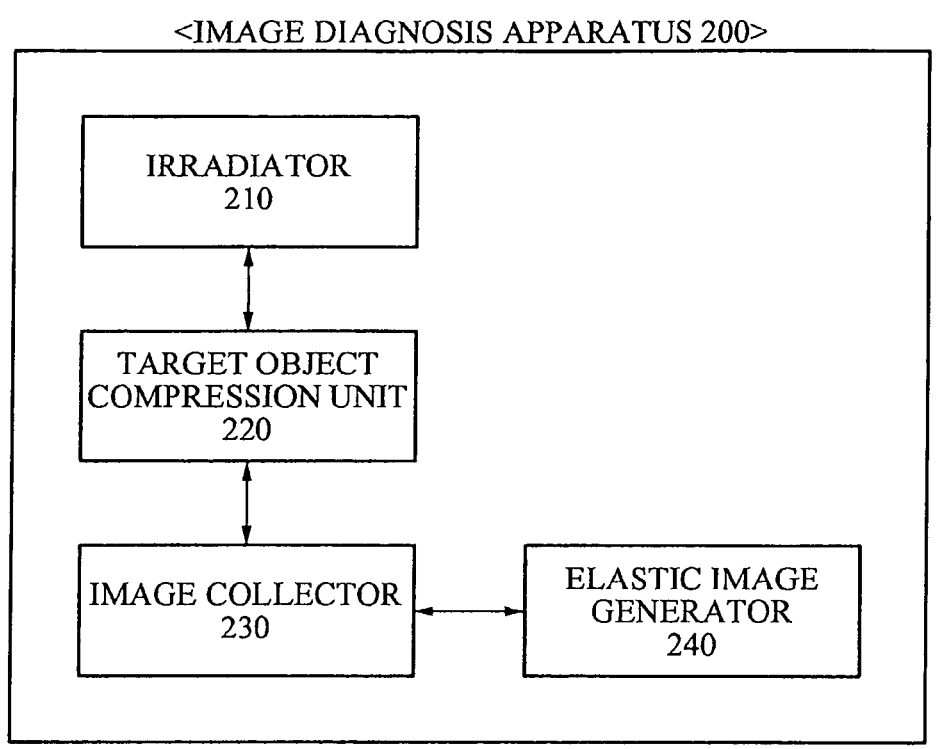
FIG. 2 is a block diagram illustrating an image diagnosis apparatus according to an embodiment.

FIG. 2 illustrates an image diagnosis apparatus 200 according to an embodiment.

The image diagnosis apparatus 200 may include an irradiator 210, a target object compression unit 220, an image collector 230, and an elastic image generator 240.

The irradiator 210 may emit radiation to a target object. The radiation may be emitted from a predetermined source, and the irradiator 210 may control the source to emit radiation to the target object. In this example, the irradiator 210 may change a location of the source to emit radiation to the target object at various angles, or may control timing of a plurality of sources to control angles of radiation emitted to the target object.

Radiation, which is particle beams and radiant rays emitted by radioactive disintegration, may be particles or electromagnetic waves emitted when elements having great atomic weight, such as uranium, plutonium, and the like, are disintegrated and changed into different elements. Throughout the specification, radiation may be X-rays or various other types of radiation.

The target object compression unit 220 may compress the target object in response to the emitted radiation. The target object compression unit 220 may control at least one press plate to compress the target object. The target object compression unit 220 may use the at least one press plate to compress the target object in multiple directions. The target object compression unit 220 may interoperate with the irradiator 210. The irradiator 210 may emit radiation to the target object at various angles at various timing. In this example, the target object compression unit 220 may appropriately control compression to the target object for each angle or for each timing. Therefore, radiation may be emitted under various conditions controlled by the irradiator 210 and the target object compression unit 220.

The image collector 230 may collect a plurality of images with respect to the compressed target object, in response to the various emitted radiation. The image collector 230 may collect the plurality of images based on the various radiation emitted to the target object.

Conditions generated by the irradiator 210 and the target object compression unit 220 to obtain the plurality of images will be described with reference to FIGS. 3 through 5.

The elastic image generator 240 may generate an elastic image with respect to the target object based on the plurality of collected images. The elastic image generator 240 may perform pre-processing and post-processing with respect to the plurality of collected images, to generate the elastic image from the plurality of images. According to the embodiments, a plurality of various high-quality images may be obtained by changing at least one of a compression intensity and characteristics of the X-ray source. According to embodiments, an elastic image with respect to the target object may be generated based on the plurality of various high-quality images and thus, lesions may be accurately and promptly detected. In this example, an emission location, an emission direction, an emission intensity, a spectrum, and the like may be changed with respect to the X-ray source.

Figure 3:
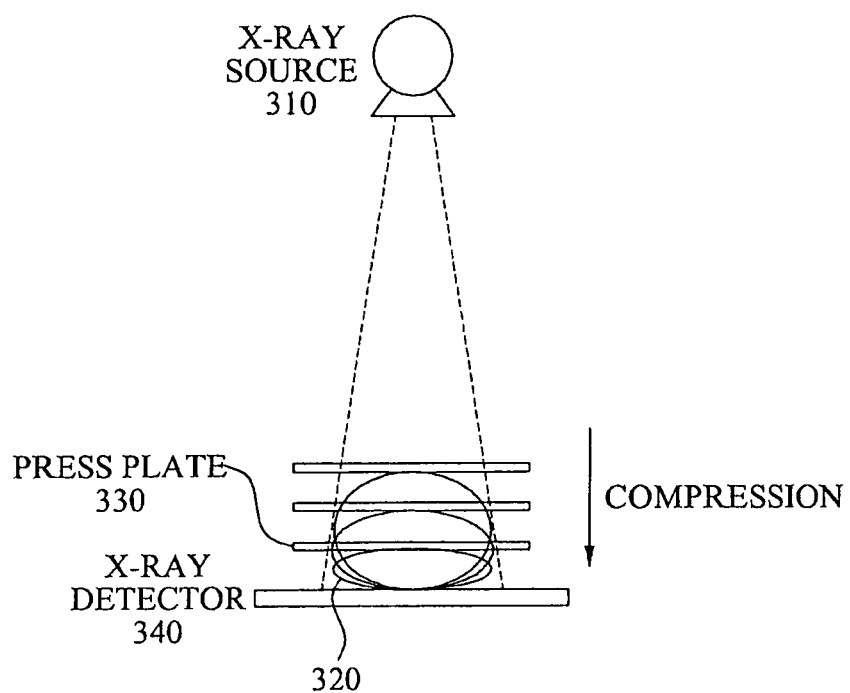
FIGS. 3, 4 and 5 are diagrams illustrating examples of generating an elastic image with respect to a target object, using an image diagnosis apparatus according to an embodiment.
Figure 4:
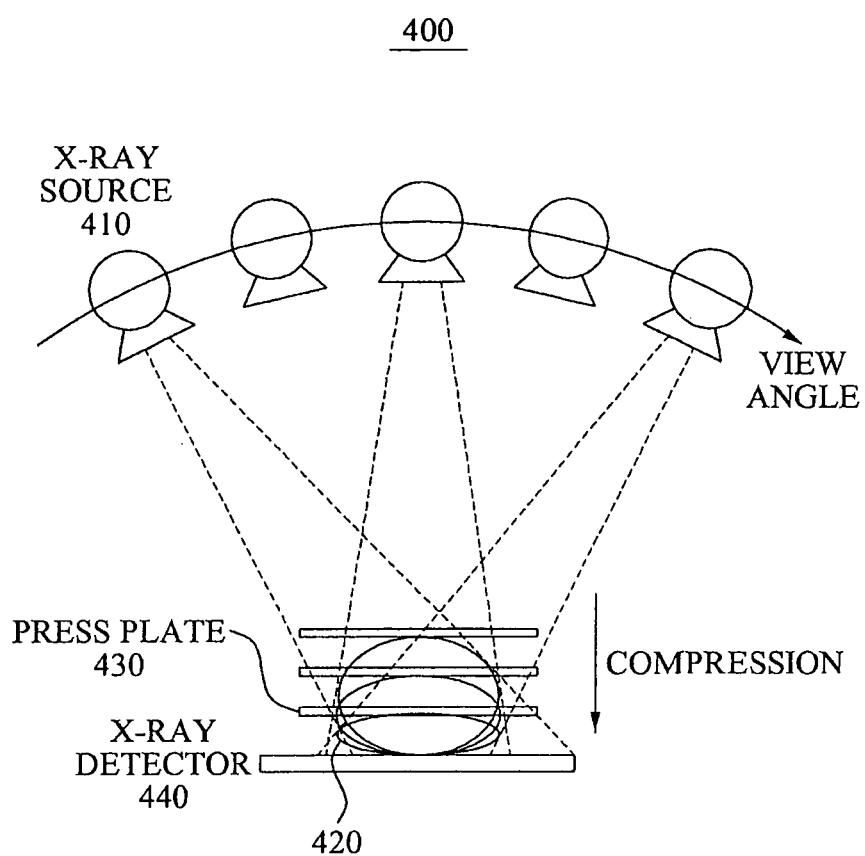
Figure 5:
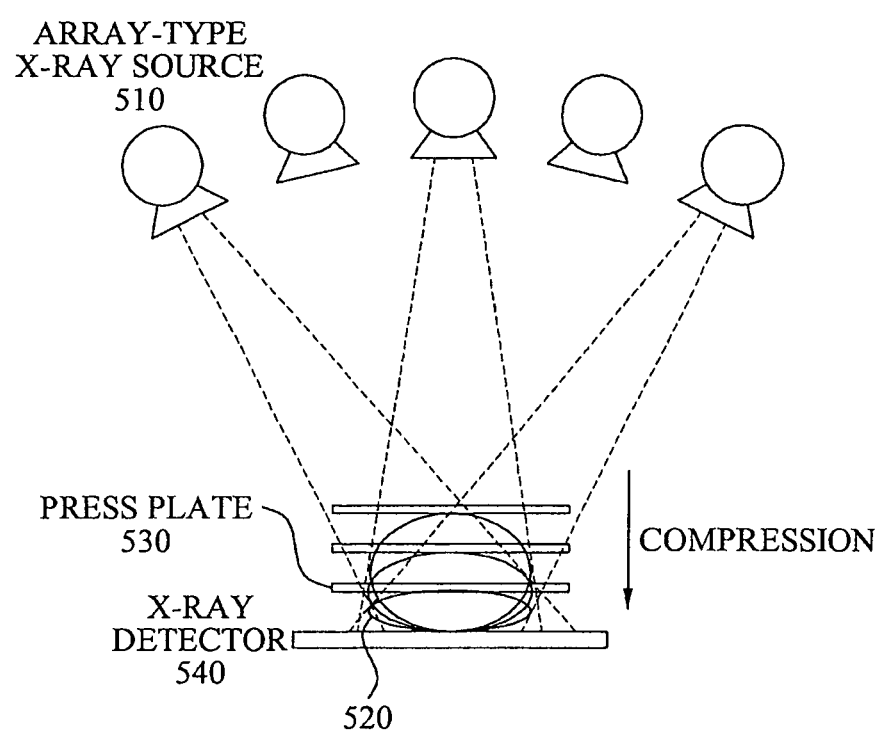

FIGS. 3 through 5 illustrate examples of generating a plurality of images with respect to a target object, using an image diagnosis apparatus according to an embodiment.

Referring to FIG. 3, there is an example of an image diagnosis apparatus 300 that generates various images with respect to the target object, as an X-ray source 310 is fixed and a compression intensity is changed. The X-ray source 310 is fixed on a gantry and the gantry of FIG. 3 may be fixed at a predetermined location.

As an example, a target object compression unit (e.g., unit 220 in FIG. 2) may change or vary the compression intensity of compression of the target object in response to emitted radiation, and an image collector may collect a plurality of images generated by the emitted radiation passing through the target object in response to the changed compression intensity.

As another example, the target object compression unit (e.g., unit 220 in FIG. 2) may change or vary a compression direction of the compression of the target object, in response to the emitted radiation, and the image collector may collect a plurality of images generated by the emitted radiation passing through the target object, in response to the changed compression direction.

An irradiator may control the gantry to enable the X-ray source 310 to emit radiation to the target object 320 at a predetermined angle from the predetermined location.

The image diagnosis apparatus 300 may fix the X-ray source 310 and may control the press plate 330 to apply various compression intensities. The image diagnosis apparatus 300 may control the press plate 330 to compress the target object 320 at different intensities.

In the example of FIG. 3, the fixed X-ray source 310 may emit radiation, at a predetermined angle, to the target object 320 compressed at different intensities, and the X-ray detector 340 may collect a plurality of images in response to the emitted radiation.

As another example, the image diagnosis apparatus 300 may control the press plate 330 to compress the target object 320 at different intensities and in different compression directions.

The image diagnosis apparatus 300 may control the compression plate 330 to diagonally compress the target object in a direction toward the X-ray detector 340, in addition to compressing the target object in a direction from the target object 320 to the X-ray detector 340.

The image diagnosis apparatus may generate an elastic image varying based on a change in the compression, using two-dimensional (2D) images with respect to the target object, which are generated based on various compressions of the target object.

The method of generating the elastic images that vary based on the change in the compression, using the 2D images obtained by various compressions, is a technology well-known to those skilled in the art and thus, a detailed description thereof will be omitted.

As an example, the image diagnosis apparatus according to an embodiment may use an algorithm, such as a mechanical (physical) modeling based registration, a deformable model based registration, a Voxel based registration, a mutual information based registration, or a volume preserving based registration, to generate an elastic image based on 2D images.

Referring to FIG. 4, there is example of an image diagnosis apparatus 400 that generates various images with respect to a target object 420, as a location of an X-ray source 410 is changed and a compression intensity is changed. The X-ray source 410 may be fixed on a gantry and may move to various locations.

An irradiator may control a movement of a radiation source to emit radiation to the target object 420 at different angles from a plurality of locations. A multi-view image collector may collect a plurality of multi-view images generated by the radiation emitted at different angles and passing through the target object 420. The multi-view image collector may be an image collector to collect images through a source in a multi-view format. Similarly, the multi-view images may be images collected through the source in the multi-view format.

As an example, the target object compression unit may control a press plate 430 to change a compression intensity of compression of the target object 420, in response to radiation emitted at different angles. The multi-view image collector may collect the multi-view images with respect to the emitted radiation, at the changed compression intensity.

As another example, the target object compression unit may control the press plate 430 to change a compression direction of the compression of the target object 430, in response to the radiation emitted at different angles. The multi-view image collector may collect the multi-view images with respect to the emitted radiation, in the changed compression directions.

The irradiator may control the gantry to move the X-ray source 410 to various locations. The irradiator may be temporally fixed at a predetermined location while the X-ray source 410 moves to various locations, and may control the X-ray source 410 to emit radiation to the target object 420. Therefore, the irradiator may control the gantry to emit radiation to the target object 420 at different angles from a plurality of different locations.

The target object compression unit may interoperate with the X-ray source 410, and may control the press plate 430 to compress the target object 420 at various compression intensities and in various compression directions.

Referring to FIG. 4, the compression intensity may be changed for each emission angle of radiation that varies based on a movement of the gantry. Therefore, when a tomosynthesis restoration is performed based on each compression intensity, an elastic image may be obtained, and the elastic image may show a change in the restored image varying based on a change in compression of the target object. When a 3D deformability is applied during an elastic image restoration process for the target object, the elastic image restoration for the target object may be more accurately performed.

An elastic image with respect to the target object is generated for each view angle varying based on the movement of the gantry, and the tomosynthesis may be applied.

When the tomosynthesis restoration is performed based on pixel deformation information obtained based on the elastic image with respect to the target object, the tomosynthesis restoration is more accurately performed. The tomosynthesis restoration may be performed with respect to a predetermined compression intensity, and the tomosynthesis restoration may be performed with respect to various compression intensities by applying the pixel deformation information. The tomosynthesis may be applied to a portion of the elastic image and thus, a total restoration time may be reduced.

An effect obtained by collecting multi-view images as illustrated in FIG. 4 may be obtained by changing a compression direction of the press plate 430 of FIG. 4.

Referring to FIG. 5, radiation may be emitted through an array-type X-ray source 510. An irradiator may control timing with respect to a plurality of array-type radiation sources located in different locations to emit radiation to the target object 520 at different angles from different locations. Therefore, a multi-view image collector may collect a plurality of images generated by the radiation emitted at different angles and passing through the target object 520.

A target object compression unit may control the press plate 530 to change at least one of a compression intensity of compression of the target object 520 or a compression direction of the compression of the target object 520, in response to the emitted radiation. The multi-view image collector may collect a plurality of multi-view images with respect to the emitted radiation under at least one of changed compression intensity and changed compression direction. For example, the array-type X-ray source 510 may emit radiation from different locations. In this example, an X-ray source does not move to change its location, and the X-ray sources, which are already set up at different locations, may be electrically switched to emit radiation.

Referring to FIG. 5, the plurality of multi-view images may be obtained by changing an emission angle and the compression intensity in the same manner as FIG. 4.

Referring to FIG. 5, an image diagnosis apparatus 500 may change the emission angle of radiation using the array-type X-ray source 510, may change the compression intensity along with the changed emission angle and thus, may collect the plurality of multi-view images.

The embodiment of FIG. 5 may emit the same amount of radiation as a conventional tomosynthesis scheme, and may estimate, based on a deformable registration scheme, a change in the target object due to the compression intensity. A degree of the change in the target object and each view angle information may need to be matched, and insufficient compression information for each view angle may be interpolated and reproduced based on multi-view images obtained from the matching.

The array-type X-ray source 510 may be orthogonally arranged and may emit radiation. In this example, overlapping multi-view images may be coded-separated.

According to embodiments, an amount of radiation emitted to a target object may be significantly reduced, and a high-quality elastic image may be obtained with a conventional radiation consumption. In addition, a number of compressions inflicting pain on the target object may be reduced by changing a compression intensity.

FIG. 6 illustrates an image diagnosis method according to an embodiment. The image diagnosis method emits radiation to a target object in operation 610, and compresses the target object in response to the emitted radiation in operation 620.

An example, the image diagnosis method controls a movement of a radiation source and to emit radiation of the target object at different angles from a plurality of locations based on the control, in operation 610

As another example, the image diagnosis method changes at least one of a compression intensity of compression of the target object and a compression direction of the compression of the target object, in response to the emitted radiation, in operation 620.

As another example, the image diagnosis method controls timing with respect to a plurality of radiation sources located in different locations, and controls the plurality of radiation sources to emit radiation to the target object at different angles from the plurality of locations based on the timing, in operation 620.

The image diagnosis method collects a plurality of images with respect to the differently compressed target object, in response to the emitted radiation, in operation 630.

The image diagnosis method generates an elastic image with respect to the target object based on the plurality of collected images in operation 640.

The method according to the above-described example embodiments may also be implemented through non-transitory computer readable code/instructions in/on a medium, e.g., a non-transitory computer readable medium, to control at least one processing element to implement any of the above-described embodiments. The medium can correspond to medium/media permitting the storing or transmission of the non-transitory computer readable code.

The non-transitory computer readable code can be recorded on or transferred to a medium in a variety of ways, with examples of the medium including recording media, such as magnetic storage media (e.g., ROM, floppy disks, hard disks, etc.) and optical recording media (e.g., CD-ROMs, or DVDs), and transmission media. The media may also be a distributed network, so that the non-transitory computer readable code is stored or transferred and executed in a distributed fashion. Still further, as only an example, the processing element could include a processor or a computer processor, and processing elements may be distributed or included in a single device. The results produced can be displayed on a display of the processing element.

In addition to the above-described embodiments, example embodiments can also be implemented as hardware, e.g., at least one hardware based processing unit including at least one processor capable of implementing any above-described embodiments.

According to example embodiments, various high-quality elastic images may be obtained by changing at least one of a compression intensity of compression to a target object and an X-ray source.

According to the example embodiments, an amount of radiation emitted to a target object may be significantly reduced and a high-quality elastic image may be obtained with a conventional radiation dose.

According to the example embodiments, a number of compressions causing pain to a target object may be reduced by changing a compression intensity.

Although a few embodiments have been shown and described, it would be appreciated by those skilled in the art that changes may be made in these embodiments without departing from the principles and spirit of the disclosure, the scope of which is defined by the claims and their equivalents.

What is claimed is:

1. An image diagnosis apparatus comprising:
   an irradiator to emit radiation to a target object under at least two different conditions of the irradiator;
   a target object compression unit to compress the target object at at least two different compression intensities corresponding to the at least two different conditions of the irradiator;
   an image collector to collect a plurality of images with respect to the compressed target object while the target object is compressed at the at least two different compression intensities; and
   an image generator to generate a composite image with respect to the target object, based on the plurality of collected images.

2. The apparatus of claim 1, wherein:
   the target object compression unit varies a compression intensity of the compression of the target object to produce a plurality of compression intensities; and
   the image collector collects the plurality of images generated by the emitted radiation passing through the target object, while the target object compression unit varies the compression intensity.

3. The apparatus of claim 2, wherein the target object compression unit varies the compression intensity of the compression of the target object in response to the emitted radiation.

4. The apparatus of claim 1, wherein:
   the target object compression unit varies a compression direction of the compression of the target object; and
   the image collector collects the plurality of images generated by the emitted radiation passing through the target object, while the target object compression unit varies the compression direction.

5. The apparatus of claim 1, wherein:
   the target object compression unit varies a compression direction of the compression of the target object, and
   the image collector collects the plurality of images generated by the emitted radiation passing through the object, while the target object compression unit varies the compression intensity and the compression direction.

6. The apparatus of claim 1, wherein:
   the irradiator controls a movement of a radiation source to emit radiation to the target object at different angles from a plurality of different locations; and
   the image collector collects the plurality of images generated by the radiation emitted at different angles and passing through the target object.

7. The apparatus of claim 6, wherein:
the target object compression unit varies the compression intensity of the compression of the target object, in response to the emitted radiation;
the image collector collects the plurality of images with respect to the emitted radiation, while the target object compression unit varies the compression intensity.

8. The apparatus of claim 6, wherein:
the target compression unit varies a compression direction of the compression of the target object, in response to the emitted radiation; and
the image collector collects the plurality of images with respect to the emitted radiation, while the target object compression unit varies the compression direction.

9. The apparatus of claim 6, wherein:
the target object compression unit varies a compression direction of the compression of the target object, and
the image collector collects the plurality of images generated by the emitted radiation passing through the object, while the target object compression unit varies the compression intensity and the compression direction.

10. The apparatus of claim 1, wherein:
the irradiator controls an emission timing with respect to a plurality of radiation sources located in different locations, to control the emission of radiation to the target object at different angles from the plurality of locations; and
the image collector collects the plurality of images generated by the radiation emitted at different angles and passing through the target object.

11. The apparatus of claim 9, wherein:
the target object compression unit varies at least one of the compression intensity and a compression direction, in response to the emitted radiation; and
the image collector collects the plurality of images with respect to the emitted radiation, while the target object compression unit varies the at least one of the compression intensity and the compression direction.

12. An image diagnosis method, the method comprising:
emitting radiation to a target object under at least two different conditions of an irradiator;
compressing the target object at at least two different compression intensities corresponding to the at least two different conditions of the irradiator;
collecting a plurality of images with respect to the compressed target object while the target object is compressed at the at least two different compression intensities; and
generating a composite image with respect to the target object based on the plurality of collected images.

13. The method of claim 12, wherein:
the compressing of the target object is in response to the emitted radiation; and
the collecting of the plurality of images with respect to the compressed target object is in response to the emitted radiation.

14. The method of claim 12, wherein:
the compressing comprises varying the compression intensity of the compression to produce a plurality of compression intensities; and
the collecting comprises collecting the plurality of images generated by emitted radiation passing through the target object while the compression intensity is varied.

15. The method of claim 12, wherein:
the compressing comprises varying a compression direction of the compression of the target object; and
the collecting comprises collecting a plurality of images with respect to the compressed target object, while the compression intensity and the compression direction are varied.

16. The method of claim 12, wherein:
the emitting comprises controlling a movement of a radiation source, and controlling the radiation source to emit radiation to the target object at different angles from a plurality of different locations; and
the collecting of the plurality of images comprises collecting the plurality of images generated by the radiation emitted at different angles and passing through the target object.

17. The method of claim 16, wherein:
the compressing comprises varying at least one of the compression intensity of the compression and a compression direction of the compression of the target object, in response to the emitted radiation; and
the collecting comprises collecting the plurality of images generated by the radiation emitted at different angles and passing through the target object.

18. The method of claim 16, wherein:
the compressing comprises varying both the compression intensity and a compression direction of the compression of the target object; and
the collecting comprises collecting a plurality of images with respect to the compressed target object, while the compression intensity and the compression direction are varied.

19. The method of claim 12, wherein:
the emitting comprises controlling an emission timing with respect to a plurality of radiation sources located in different locations, and controlling the emission to emit, to the target object, radiation at different angles from the plurality of different locations based on the timing; and
the collecting comprises collecting the plurality of images generated by the radiation emitted at different angles and passing through the target object.

20. The apparatus of claim 1, wherein the target object compression unit varies a compression direction of the compression of the target object with respect to the at least two different compression intensities.

* * * * *